United States Patent [19]

Michl et al.

[11] 4,439,380

[45] Mar. 27, 1984

[54] PHOTOPOLYMERIZABLE COMPOSITION, ESPECIALLY FOR DENTAL PURPOSES

[75] Inventors: Rudy Michl, Schaan; Hanspeter Willi, Vaduz, both of Liechtenstein

[73] Assignee: Etablissement Dentaire Ivoclar, Schaan, Liechtenstein

[21] Appl. No.: 284,294

[22] Filed: Jul. 17, 1981

[30] Foreign Application Priority Data

Aug. 1, 1980 [DE] Fed. Rep. of Germany ....... 3029276

[51] Int. Cl.³ .................... C08F 2/50; A61C 13/00; A61C 13/08
[52] U.S. Cl. ............................. 264/16; 204/159.23; 264/17; 264/19; 264/22; 433/202; 433/226; 433/228; 523/115
[58] Field of Search ................. 204/159.23; 264/22, 264/16, 17, 19; 433/202, 226, 228

[56] References Cited

U.S. PATENT DOCUMENTS

| | | | |
|---|---|---|---|
| 3,864,133 | 2/1975 | Hisamatsu et al. | 204/159.23 |
| 4,001,304 | 1/1977 | Nyi et al. | 204/159.23 |
| 4,071,424 | 1/1978 | Dart et al. | 204/159.23 |
| 4,089,763 | 5/1978 | Dart et al. | 204/159.24 |
| 4,115,232 | 9/1978 | Nyi et al. | 204/159.24 |
| 4,277,319 | 7/1981 | Nyi et al. | 204/159.23 |

*Primary Examiner*—John C. Bleutge
*Assistant Examiner*—Arthur H. Koeckert

*Attorney, Agent, or Firm*—Sprung, Horn, Kramer & Woods

[57] ABSTRACT

Photopolymerizable composition, especially for dental purposes, which contains as photopolymerizable olefin compounds especially acrylic and/or methacrylic compounds as well as a ketone and an amine as activating substances. The amine has the general formula

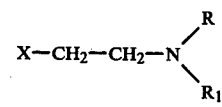

wherein the symbols have the following meanings:
X represents cyan or halogen,
R represents the group X—CH₂—CH₂-, an alkyl group of 1 to 6 carbon atoms, or a hydroxyl group of 2 to 6 carbon atoms, an acrylic, methacrylic or vinyl group, and
R₁ represents a substituted or unsubstituted phenyl, benzyl or styryl radical, or
R and R₁ together form an alkylene group of 4 to 5 carbon atoms, the amine being able to be present also in polymeric form if in the monomer R represents an acrylic, methacrylic or vinyl group and/or R₁ represents the styryl radical.

22 Claims, No Drawings

PHOTOPOLYMERIZABLE COMPOSITION, ESPECIALLY FOR DENTAL PURPOSES

BACKGROUND OF THE INVENTION

1. Field of the Invention

The invention relates to photopolymerizable compositions, especially for dental purposes, containing photopolymerizable olefin compounds, especially acrylic and/or methacrylic compounds, as well as at least one ketone and one amine as activating substances.

2. Discussion of Prior Art

Photopolymerizable compositions on the basis of olefin compounds, especially acrylic and/or methacrylic compounds are known, which contain $\alpha,\alpha$-diketones which absorb visible light in the wavelength range of 300 to 500 nm. Important representatives of these ketones are benzophenone, benzil and camphorquinone. One important field for the application of these photopolymerizable compositions is dentistry.

In the preparation of, for example, varnishes, paper coatings or dental fillings, the photopolymerizable compositions can be catalyzed only with these ketones and can be set by visible light. Relatively thin layers are set in this manner, and this takes a relatively long time. To shorten the setting time, it is known to add to the photopolymerizable compositions, in addition to the ketones, amines having CH groups in the alpha position. Examples of such amines are triethanolamine, dimethylaminoethanol and dimethylaminoethylmethacrylate.

These amines have a disagreeable odor; furthermore, their toxicity and their relatively weak accelerating or activating action are disadvantageous. In general, they produce approximately only a doubling of the rate of reaction.

Amines such as N,N-dimethylaniline, N,N-dimethyl-p-toluidine or N,N-dimethyl-sym.-xylidine, have a definitely better accelerating action in the photopolymerizable compositions. However, the addition of these substances often results in a severe brown discoloration of the polymer. Even in this case the accelerating action is not yet satisfactory.

THE INVENTION

It is the object of this invention to provide photopolymerizable compositions of the kind defined above, which can easily be set, so that, for example, even relatively opaque compositions charged with filler can be cured in a short time and in relatively thick layers, without producing disagreeable odors.

This object is achieved in accordance with the invention by photopolymerizable compositions which are characterized in that they contain an amine of the general formula

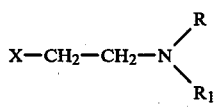

wherein the symbols have the following meaning:
X represents cyan, or halogen, such as, chlorine, bromine or iodine,
R represents the group X—CH$_2$—CH$_2$— (wherein X has the same meaning as given above), an alkyl group having 1 to 6 carbon atoms, or a hydroxyalkyl group with 2 to 6 carbon atoms, or an acrylic, methacrylic or vinyl group,
R$_1$ represents a phenyl or benzyl or styryl moiety substituted, if desired, by chlorine, bromine or iodine, or by carboxy, carbalkoxy, low alkyl, alkoxy or hydroxyalkyl, cyano or nitro groups, or
R and R$_1$ together form an alkylene group of 4 or 5 carbon atoms, the amine being able to be present also in polymeric form, if in the monomer R represents an acrylic, methacrylic or vinyl group and/or R$_1$ represents the styryl radical.

The photopolymerizable compositions especially satisfy the requirements of dental plastics. The rate of polymerization of these compositions is approximately quadrupled as compared with the use of the ketones mentioned, and this is especially important when dental plastics, such as dental fillings, are to be hardened in the patient's mouth by photopolymerization. The photopolymerizable dental plastic compositions generally contain fillers and coloring pigments, which greatly weaken the intensity of the light used for the polymerization. The term, "dental plastic compositions," as used herein, is to be understood to apply not only to dental filling materials and cements, but also to compositions for producing artificial teeth, crowns and bridges, as well as artificial dentures, in which these compositions can be set by photopolymerization outside of the mouth.

The photopolymerizable compositions, however, can also be used in other fields of technology and medical practice, wherever rapid setting is important. Examples of such applications are to be found in the printing, paint, photography and copying industries, in which plastic coatings are to be cured as rapidly as possible.

Of the amines used in the compositions of the invention, those are preferred in which X represents cyan or chlorine; furthermore, R represents preferably a low alkyl group of 1 to 5 carbon atoms, especially the methyl group. R$_1$ is preferably a phenyl radical.

Examples of suitable 2-cyanoethylamine derivatives are N-methyl-N-cyanoethylaniline, N,N-di-(2-cyanoethyl)-aniline, N,N-di-(2-cyanoethyl)-m-toluidine and the like. In these examples, R$_1$ represents a simple phenyl radical or one substituted by only one methyl group. Examples of compounds in which R and R$_1$ together form an alkylene group of 4 and 5 carbon atoms are N-(2-cyanoethyl)-pyrrolidine and N-(1-cyanoethyl)-piperidine.

If the amines are themselves in polymeric form they generally have up to 1000 repeating units, preferably up to 200 repeating units.

An example in which the phenyl radical of R$_1$ is replaced by a benzyl radical is N,N-di-(2-cyanoethyl)-benzylamine. In this class of compounds the substituent is not, of course, limited to the cyanoethyl group, but can include any of the above-named groups.

Examples of amines of the 2-cyanoethyl type, in which the radical R$_1$ represents a substituted phenyl radical, are N,N-di-(2-cyanoethyl)-halogen anilines, such as N,N-di-(2-cyanoethyl)-4-chloraniline, N,N-di-(2-cyanoethyl)-3,5-dichloraniline and N,N-di-(2-cyanoethyl)-2,6-dichloraniline, as well as the N-alkyl-N-(2-cyanoethyl)-halogen anilines, such as N-methyl-N-(2-cyanoethyl)-4-chloraniline, N-methyl-N-(2-cyanoethyl)-3,5-dichloraniline, and N-methyl-N-(2-cyanoethyl)-2,6-dichloraniline.

In this group of compounds, the phenyl moiety can also be substituted by alkyl groups. Examples of such compounds are N,N-di-(2-cyanoethyl)-alkylanilines, such as N,N-di-(2-cyanoethyl)-4-methylaniline, N,N-di-(2-cyanoethyl)-3,5-dimethylaniline, N,N-di-(2-cyanoethyl)-2,6-dimethylaniline, as well as N-alkyl-N-(2-cyanoethyl)-alkylanilines such as N-methyl-N-(2-cyanoethyl)-4-methylaniline, N-methyl-N-(2-cyanoethyl)-3,5-dimethylaniline and N-methyl-N-(2-cyanoethyl)-2,6-dimethylaniline.

The alkyl substituents can in this case be branched or straight-chain alkyls. Other substituents on the phenyl radical $R_1$ are bromine or iodine, carboxy or carbalkoxy groups, low alkoxy or hydroxyalkyl groups, or cyano or nitro groups. These can be at any desired substitution point. The alkyl groups of $R_1$ alkyl containing moieties can have 1–5 carbon atoms.

Examples of suitable 2-halogen-ethylamine derivatives are N-(2-chloroethyl)N-methylaniline, N-(2-bromomethyl)N-methylaniline, N,N-di-(2-chloroethyl)-aniline, N,N-di-(2-bromoethyl)-aniline, N,N-di-(2-chloroethyl)-m-toluidine and N,N-di-(2-bromoethyl)-m-toluidine. In these examples, $R_1$ represents a simple phenyl moiety or one substituted by a methyl group.

Examples of amines in which R and $R_1$ together form an alkylene group of 5 carbon atoms are N-(2-chloroethyl)-piperidine and N-(2-bromoethyl)-piperidine.

Examples in which $R_1$ represents a benzyl radical are N,N-di-(2-chloroethyl)-benzylamine and N,N-di-(2-bromoethyl)-benzylamine.

Additional examples of 2-halogen-ethylamine derivatives in which $R_1$ represents a substituted phenyl radical are N,N-di-2-halogenethyl)-alkylanilines, such as N,N-di-(2-chloroethyl)-4-methylaniline, N,N-di-(2-chloroethyl)-3,5-dimethylaniline and N,N-di-(2-chloroethyl)-2,6-dimethylaniline, as well as N-alkyl-N-(2-chloroethyl)-alkylanilines such as N-methyl-N-(2-chloroethyl)-4-methylaniline, N-methyl-N-(2-chloroethyl)-3,5-dimethylaniline and N-methyl-N-(2-chloroethyl)-2,6-dimethylaniline.

In the case of the 2-halogen-ethylamine derivatives, higher branched or straight-chain alkyl moieties can be used as alkyl substituents, both on the nitrogen atom and on the phenyl moiety, and likewise the corresponding hydroxyalkyl moieties. It is furthermore possible to use as substituents on the phenyl or benzyl moiety, iodine, carboxy groups, carbalkoxy groups, alkoxy groups, cyano groups or nitro groups at any desired substitution point.

The conventional photopolymerizable olefin compounds, especially the acrylic and/or methacrylic compounds, can be used as monomers, preferably the following compounds:

ethyleneglycoldimethacrylate,
butanediol-1,4-dimethacrylate,
triethyleneglycoldimethacrylate,
dodecanediol-1,12-dimethacrylate,
decanediol-1,10-dimethacrylate,
2,2-bis[-p(γ-methacryloxy-β-hydroxypropoxy)-phenyl]-propane,
di-adduct of 2-hydroxyethylmethacrylate and trimethylhexamethylenediisocyanate,
di-adduct of 2-hydroxyethylmethacrylate and isophorone diisocyanate,
trimethylolpropane trimethacrylate,
pentaerythritol trimethacrylate,
pentaerythritol tetramethacrylate.

The acrylates of the said compounds can also be used instead of the methacrylates.

Examples of other suitable olefin compounds which can be used in the polymerizable compositions are unsaturated polyesters, i.e., mixed condensates of unsaturated carboxylic acids and polyvalent alcohols, in combination with methacrylates if desired.

Fillers can also be used to the photopolymerizable compositions. For dental purposes, these are especially inert, inorganic fillers, such as for example the oxides of aluminum and silicon, silicate glasses, calcium carbonate and others. Excellent fillers are the pyrogenic silicas, whose BET surface area can be between 30 and 400 $m^2/g$. Basically, however, it is also possible to use fillers which are produced by precipitation. While the average grain size of the primary particles in the pyrogenically produced fillers does not exceed an upper limit of 70 nm, particle sizes up to 10 μm, especially up to 1 μm, are possible.

In the photopolymerizable compositions in accordance with the invention, the activating substances, namely the ketones and amines, are generally contained in amounts of about 0.05 to 70% by weight of the entire composition. The stated upper limit can be reached if a polymerizable amine is selected, i.e., one in which R represents an acrylic, methacrylic or vinyl group and/or $R_1$ represents a styryl group. Such an amine can first be polymerized by itself, and then the photopolymerizable composition can be added to it. However, it can also be photopolymerized in its monomeric form together with the photopolymerizable olefin compounds, the ketone or diketone serving in both cases as catalyst. Even in the polymeric form, these amines still have an accelerating action. Preferably, the activating substances are used in amounts of about 0.05 to 5% by weight. Special ranges lie between 0.1 and 3%, especially between 0.2 and 0.8 weight-percent. The ketone, or α,α-diketone as the case may be, is usually present in amounts of about 5 to 45%, preferably in amounts of about 10 to 35%, of the weight of the entire activating substance. Substituted benzophenones and benzils can be used as ketones or α,α-diketones, preferable compounds, however, are benzophenone, benzil and/or camphorquinone.

The photopolymerizable compositions advantageously contain as activating substances a mixture of N-methyl-N-cyanoethylaniline and D,L-camphorquinone.

The photopolymerizable compositions are preferably prepared and hardened in the following manner.

A paste is prepared by mixing together the following substances in a mixing apparatus:

One or more polymerizable methacrylates, a filler in powder form which can be either organic or inorganic, and an activating substance, e.g., a mixture of N-methyl-n-cyanoethylaniline and D,L-camphorquinone, plus pigments if desired. This paste is photosensitive, and is used as a filling material by the dentist, for example. It is stored in opaque containers. After the dentist has prepared a cavity, the paste is placed in it and molded as desired. Then the paste is irradiated for about 20 to 60 seconds with a halogen cold light, and thus polymerized.

The same paste, or others of different composition, can be used for modeling crowns and bridgework. The polymerization is then performed in a pressure polymerization apparatus which is filled with water, for example, and must be such that the polymerizable composition can be hardened by means of light. For this purpose the apparatus consists at least partially of glass, for example.

The invention will be explained by the following examples, which are not limitative. The camphorquinone in each case is of the D,L type.

EXAMPLE 1

To test various photopolymerizable compositions for their rate of reaction, the activators were dissolved in a mixture of 80 wt.-% of a di-adduct of 2-hydroxyethyl-methacrylate and trimethylhexamethylene diisocyanate, and 20 wt.-% of triethyleneglycol dimethacrylate.

Specifically, D,L-camphorquinone and triethanolamine, camphorquinone and N-methyl-N-2-cyanoethylaniline, and camphorquinone and N,N-dimethyl-p-toluidine, were incorporated into the photopolymerizable compositions, a concentration of 0.01 mol per kg being maintained in each case. This corresponds, for example, to 1.66 g of camphorquinone per kg and 3.2 g of N-methyl-N-cyanoethylaniline per kg of solution. The photopolymerizable compositions were irradiated in small plastic cells (8 mm high, 16 mm in diameter) at a distance of 10 cm from a 20-watt halogen lamp (Osram 41900). The polymerization time was determined with a stopwatch and a fine spatula, the end of the polymerization being determined as follows:

At intervals of 4 seconds, the spatula was pressed into the sample. The end of the polymerization is indicated by the fully hardened surface.

The polymerization time was as follows:
1. for camphorquinone alone 96 sec.
2. for camphorquinone+triethanolamine 48 sec.
3. for camphorquinone+N,N-dimethyl-p-toluidine 30 sec.
4. for camphorquinone+N-methyl-N-(2-cyanoethyl)-aniline 24 sec.

Sample 4 was furthermore virtually odorless, while samples 2 and 3 had a disagreeable odor.

EXAMPLE 2

The methacrylate mixture used in Example 1, containing 0.01 mol of camphorquinone per kg and 0.01 mol of activator per kg, was mixed with 75% by weight, of finely ground quartz powder of the kind commonly used for tooth filling materials. In addition, 0.2% of titanium dioxide paste ("Irgalith Dispers Weiss 1123, Ciba Geigy") was mixed in to achieve a translucence of 28%.

This photosensitive paste is then put into a test mold of polyoxymethylene of the following construction: two pieces measuring 40×30×15 mm, one of them having on its largest surface an open-ended groove of 3.5×3.5 mm. The two pieces are held together by means of a C-clamp so as to form a block measuring 40×30×30 mm in whose center is a cavity measuring 3.5×3.5 mm.

After the test mold is filled, the paste is irradiated in the direction of the axis of the cavity for 20 seconds with blue light from a fiber optic halogen lamp (Pluraflex HL 150 made by Litema, Munich). Then the mold is opened and the depth of the hardened material is measured with a caliper gauge. The depth of the hardened material is as follows:

Paste No. 1—camphorquinone alone: 0.9–1.1 mm
Paste No. 2—camphorquinone+triethanolamine: 1.9–2.1 mm
Paste No. 3—camphorquinone+N,N-dimethyl-3,5-xylidine: 4.2–4.5 mm
Paste No. 4—camphorquinone+N(2-cyanoethyl)N-methylaniline: 4.8–5.2 mm Pastes Nos. 1 to 3 are less thoroughly hardened than paste No. 4, which indicates the higher activity of the amine used in it. Furthermore, pastes Nos. 2 and 3 have a very unpleasant odor, while pastes 1 and 4 are virtually odorless.

Test samples were prepared with the above-described pastes using irradiation by halogen light (circular disks of 1 mm thickness and 10 mm diameter). These disks were immersed in distilled water for 3 weeks at 60° C. The sample made from paste No. 3 had a strong brown discoloration, while the one made from paste No. 2 was only slightly discolored. The samples made from pastes Nos. 1 and 4 were not discolored.

EXAMPLE 3

Other activator combinations were used in the same procedures as in Example 2. The results are given in Table I.

TABLE I

| Initiator | Activator | Odor | Depth of polymerization mm | Discoloration after 3 weeks in 60° C. distilled water |
|---|---|---|---|---|
| Camphorquinone | N,N—dimethylbenzylamine | disagreeable | 4.8–5.1 mm | brownish yellow |
| Camphorquinone | N,N—di(2-cyanoethyl)-aniline | odorless | 4.6–4.8 mm | no discoloration |
| Camphorquinone | N,N—dimethylamino-adamantane | slight amine odor | 3.1–3.3 mm | no discoloration |

EXAMPLE 4

A polymerizable mixture is prepared from the following components:
- 37.5 wt.-% of 2,2-bis[p-(γ-methacryloxy-β-hydroxypropoxy)-phenyl]propane
- 25 wt.-% of a di-adduct of 2-hydroxyethylmethacrylate and trimethylhexamethylenediisocyanate
- 37.5 wt.-% of triethyleneglycoldimethacrylate.

To this polymerizable mixture is added 0.25% of camphorquinone and 0.75% of an amine indicated in the following table. 60 wt.-% of this mixture is mixed with 40 wt.-% of a pyrogenic silica (Aerosil OX 50 made by Degussa) having a BET surface area of 50 m$^2$/g. By vigorous stirring, a viscous mass is obtained. A portion of this viscous mass is taken, 1% of benzoyl peroxide is added to it, and the whole is polymerized for 12 h at 100°. Then, by thorough crushing, a polymer filler is obtained which itself contains the inorganic filler.

This polymer filler is mixed with the initially prepared viscous mass in a ratio of 1:1 by weight in a suitable kneader, and a uniform paste is obtained. To achieve a translucence of 28%, 0.2% of a titanium dioxide paste was added during the mixture. With this paste, tests were made of the hardening depth and discoloration as in Example 2. The results are given in Table II.

TABLE II

| Initiator | Activator | Depth of polymerization in mm | Discoloration after 3 weeks in 60° C. distilled water | Odor |
|---|---|---|---|---|
| Camphorquinone | — | 1.2–1.4 | none | — |
| Camphorquinone | triethanolamine | 2.0–2.2 | negligible | disagreeable |
| Camphorqunone | N,N—dimethyl-3,5-xylidine | 4.5–4.8 | browninsh yellow | disagreeable |
| Camphorquinone | N—(2-cyanoethyl)-N—methylaniline | 4.8–5.4 | none | odorless |

What is claimed is:

1. A photopolymerizable composition comprising a photopolymerizable olefin, at least one ketone and one amine, said amine having the formula

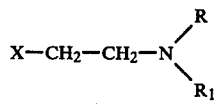

wherein the symbols have the following meaning:
X represents cyan, chlorine, bromine or iodine; R represents the group X—CH₂—CH₂ (where X has the meaning given above) or an alkyl group of 1 to 6 carbon atoms or a hydroxy alkyl group of 2 to 6 carbon atoms;
R₁ represents a benzyl, phenyl or styryl radical optionally substituted by chlorine, bromine or iodine, or by a carboxy, carbalkoxy, lower alkyl, alkoxy or hydroxyalkyl, cyano or nitro group.

2. A photopolymerizable composition according to claim 1 wherein X represents cyan.

3. A photopolymerizable composition according to claim 1 wherein R represents an alkyl radical of 1 to 5 carbon atoms and R₁ represents the phenyl radical.

4. A photopolymerizable composition according to claim 1 wherein R represents methyl.

5. A photopolymerizable composition according to claim 1 containing 1 or more α,α-diketones.

6. A photopolymerizable composition according to claim 1 wherein said amine is present in an amount of 0.05 to 5% by weight, based upon the total weight of the composition.

7. A composition according to claim 6 wherein said composition contains one or more α,α-diketones which is present in an amount of 5 to 45 weight percent based upon the weight of said amine.

8. A composition according to claim 1 wherein said diketone is benzil and/or camphorquinone.

9. A composition according to claim 1 wherein said ketone is D,L-camphorquinone and said amine is N-methyl-N-cyanoethylaniline.

10. A composition according to claim 1 containing at least one filler.

11. A composition according to claim 1 wherein said amine is selected from the group consisting of N-methyl-N-cyanoethylaniline, N,N-di-(2-cyanoethyl)-aniline, N,N-di-(2-cyanoethyl)-m-toluidine, N,N-di-(2-cyanoethyl)-benzylamine, N,N-di-(2-cyanoethyl)-4-chloraniline, N,N-di-(2-cyanoethyl)-3,5-dichloraniline, N,N-di-(2-cyanoethyl)-2,6-dichloraniline, N-methyl-N-(2-cyanoethyl)-4-chloraniline, N-methyl-N-(2-cyanoethyl)-3,5-dichloraniline, N-methyl-N-(2-cyanoethyl)-2,6-dichloraniline, N,N-di-(2-cyanoethyl)-4-methylaniline, N,N-di-(2-cyanoethyl)-3,5-dimethylaniline N,N-di-(2-cyanoethyl)-2,6-dimethylaniline, N-methyl-N-(2-cyanoethyl)-4-methylaniline, N-methyl-N-(2-cyanoe-thyl)-3,5-dimethylaniline, N-methyl-N-(2-cyanoethyl)-2,6-dimethylaniline, N-(2-chloroethyl)N-methylaniline N-(2-bromoethyl)N-methylaniline, N,N-di-(2-chloroethyl)-aniline, N,N-di-(2-bromoethyl)-aniline, N,N-di-(2-chloroethyl)-m-toluidine, N,N-di-(2-bromoethyl)-m-toluidine, N,N-di-(2-chloroethyl)-benzylamine, N,N-di-(2-bromoethyl)benzylamine, N,N-di-(2-chloroethyl)-4-methylaniline, N,N-di-(2-chloroethyl)-3,5-dimethylaniline, N,N-di-(2-chloroethyl)-2,6-dimethylaniline, N-methyl-N-(2-chloroethyl)-4-methylaniline, N-methyl-N-(2-chloroethyl)-3,5-dimethylaniline and N-methyl-N-(2-chloroethyl)-2,5-dimethylaniline.

12. A composition according to claim 1 wherein said amine is itself in the form of a polymer.

13. A photopolymerizable composition according to claim 1 wherein said photopolymerizable olefin is an acrylic or methacrylic compound.

14. A composition according to claim 1 wherein said polymerizable olefin is an di-adduct of 2-hydroxyethylmethacrylate and trimethylhexamethylene diisocyanate.

15. A composition according to claim 14 wherein said di-adduct is in admixture with triethyleneglycol dimethacrylate.

16. The composition of claim 15 additionally containing quartz as filler.

17. A composition according to claim 1 containing D,L-camphorquinone as ketone and N,N-di-(2-cyanoethyl)-aniline.

18. A polymerizable composition according to claim 1 wherein said polymerizable olefin comprises 2,2-bis[p-(γ-methacryloxy-β-hydroxypropoxy)-phenyl]propane and a di-adduct of 2-hydroxyethylmethacrylate and trimethylhexamethylenediisocyanate and triethyleneglycoldimethacrylate.

19. A polymerizable composition according to claim 1 wherein said ketone comprises camphorquinone and said amine is N-(2-cyanoethyl)-N-methylaniline.

20. In a process of filling a dental cavity with a dental filling composition, the improvement which comprises employing as the dental filling composition a composition according to claim 1 and thereafter photopolymerizing the composition.

21. In a process of forming a dental crown, bridgework or other dental prosthetic device by molding the same employing a photopolymerizable molding composition, the improvement which comprises employing as the photopolymerizable molding composition the composition of claim 1 and thereafter photopolymerizing the composition.

22. A photopolymerizable composition according to claim 1 wherein the said amine is N-methyl-N-(2-cyanoethyl) aniline.

* * * * *